(12) United States Patent
Shotey et al.

(10) Patent No.: US 8,372,349 B1
(45) Date of Patent: Feb. 12, 2013

(54) AIR FRESHENER

(76) Inventors: Marcus J. Shotey, Scottsdale, AZ (US); John Klein, Gilbert, AZ (US)

( * ) Notice: Subject to any disclaimer, the term of this patent is extended or adjusted under 35 U.S.C. 154(b) by 200 days.

(21) Appl. No.: 13/013,351

(22) Filed: Jan. 25, 2011

Related U.S. Application Data

(60) Provisional application No. 61/298,981, filed on Jan. 28, 2010.

(51) Int. Cl.
*A61L 9/00* (2006.01)
*A62B 7/08* (2006.01)
*B08B 3/04* (2006.01)
*B01D 41/00* (2006.01)

(52) U.S. Cl. .................. 422/306; 134/104.1; 134/166 R; 134/172; 134/198; 96/222; 96/290; 55/468; 55/482; D23/351; D23/366

(58) Field of Classification Search .................. 422/1, 5, 422/124, 306; 134/104.1, 166 R, 172, 198; 96/222, 290; 55/468, 482; D23/351, 355, D23/365–366, 370
See application file for complete search history.

(56) References Cited

U.S. PATENT DOCUMENTS

| | | | |
|---|---|---|---|
| 4,157,787 A | 6/1979 | Schwartz | |
| 4,277,014 A | 7/1981 | Webinger | |
| 5,034,222 A | 7/1991 | Kellett et al. | |
| 5,361,522 A | 11/1994 | Green | |
| 5,498,397 A | 3/1996 | Horng | |
| D458,359 S | 6/2002 | Blanchette | |
| 7,244,398 B2 | 7/2007 | Kotary et al. | |
| 2005/0285538 A1* | 12/2005 | Jaworski et al. | 315/76 |

\* cited by examiner

*Primary Examiner* — Jill Warden
*Assistant Examiner* — Monzer Chorbaji
(74) *Attorney, Agent, or Firm* — Booth Udall Fuller, PLC

(57) ABSTRACT

An air freshener including a housing having a reservoir chamber, a dispenser, a pump intermediate the reservoir and the dispenser, a pad, at least one fan proximate the pad, and wherein the dispenser transfers a scented liquid onto the pad and the at least one fan directs air flow proximate the pad.

15 Claims, 1 Drawing Sheet

AIR FRESHENER

CROSS-REFERENCE TO RELATED APPLICATIONS

This application claims priority to earlier patent application entitled "Air Freshener," Ser. No. 61/298,981 filed Jan. 28, 2010, the disclosure of which is hereby incorporated herein by reference.

BACKGROUND

1. Technical Field

This invention generally relates to air fresheners and particularly refillable devices for freshening the air in a particular area.

2. Background Art

Air fresheners are known to come in a variety of forms, including chemical compositions which are activated by the air, fan operated devices which push or pull a scent into a room, and cardboard type materials which provide a scent in the air. The cardboard type materials are similar to an automotive tree air freshener which emits a scent and the freshener's effectiveness steadily decreases over time until the air freshener is nothing more than a decorative element. Chemical compositions may include gels or similar compositions which are absorbed into the air to mask any odors. The fan operated devices may be battery or outlet powered and pushes or pulls air across a scented portion of the device and into the surrounding area. The scented portion may be connected to a scented oil for absorption and the fan speed may be adjusted to vary the strength of the scent within the room.

SUMMARY

Aspects of this document relate to an air freshener. In one aspect, an air freshener including a housing having a reservoir chamber, a dispenser, a pump intermediate the reservoir and the dispenser, a pad, at least one fan proximate the pad, and wherein the dispenser transfers a scented liquid onto the pad and the at least one fan directs air flow proximate the pad.

Particular implementations may include one or more of the following features. The at least one fan may be directed at the pad. The dispenser may be located above the pad. The channel may connect the reservoir chamber and the dispenser. The pump may be located within the channel. The at least one fan may be a pair of fans located below the pad. The reservoir chamber may further include a refill opening.

Additional implementations may include one or more of the following features. The pump and the at least one fan may be powered by a source selected from the group consisting of batteries, photovoltaic cells, and an alternating current adapter. The air freshener may further include a controller regulating a speed of the at least one fan and the fluid flow rate of the dispenser. The pad may be replaceable. The reservoir chamber may further include a low level sensor to turn off the pump when a low level condition is detected. The at least one fan may oscillate. The dispenser may be located above the pump. The dispenser may be located above the reservoir. The dispenser may be movable. Moving the dispenser to a position above the at least one fan increases a strength of a scent.

BRIEF DESCRIPTION OF THE DRAWINGS

Embodiments of the disclosure will hereinafter be described in conjunction with the appended drawing, where like designations denote like elements, and.

DESCRIPTION

Figure 1:
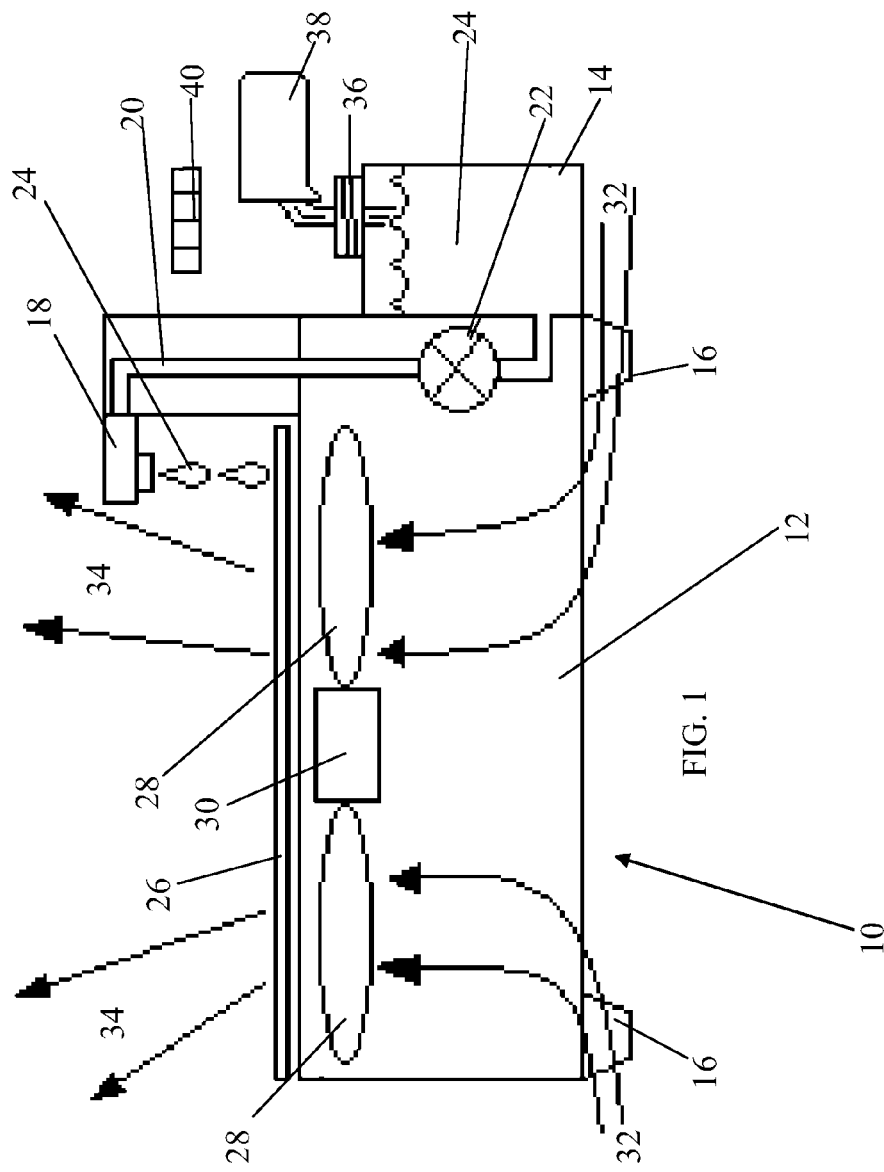
FIG. 1 is a view of an air freshener.

This disclosure, its aspects and implementations, are not limited to the specific components or assembly procedures disclosed herein, as virtually any components consistent with the intended structure and operation of an air freshener may be utilized. Many additional components and assembly procedures known in the art consistent with the intended air freshener will become apparent for use with particular implementations from this disclosure. Accordingly, for example, although particular implementations are disclosed, such implementations and implementing components may comprise any shape, size, style, type, model, version, measurement, concentration, material, quantity, and/or the like as is known in the art for such air fresheners and implementing components, consistent with the intended operation.

Implementations of an air freshener relate to an air freshener with a dispenser and pad. Particular implementations include a pump and reservoir with a replaceable pad and at least one fan. The various implementations may be manufactured using conventional procedures known to those of ordinary skill in the art as added to and improved upon through the procedures described herein.

Referring to FIG. 1, a view of an air freshener implementation is shown. The air freshener 10 includes a housing assembly 12 with a reservoir chamber 14 attached thereto. Both the housing assembly 12 and the reservoir chamber 14 may rest atop mounting fee 16. In one aspect, reservoir chamber 14 is located adjacent and on one side of housing assembly 12, however reservoir chamber 14 may be located in any position, including below or above the housing assembly or on any or multiple sides of the housing assembly without departing from the spirit of the disclosure.

Air freshener 10 also includes a dispenser 18 connected to reservoir chamber 14 through a channel 20. Channel 20 may include a pump 22 inline within the channel intermediate dispenser 18 and reservoir chamber 14. Pump 22 is arranged to move a scented liquid 24 from reservoir chamber 14 to dispenser 18 as required. Specifically, a controller (not shown) may control the speed at which pump 22 operates to selectively increase or decrease the amount of scented oil located on a pad 26. While the pump is shown and described as being within channel 20, the pump may be located outside of the channel without departing from the disclosure and any suitable pumping method may be utilized.

A pair of fans 28 are located within housing assembly 12 and are preferably located near a top portion of housing assembly 12. Fans 28 may be powered by a motor 30 and both the fans 28 and motor 30 are located proximate pad 26. In one aspect, fan 28 is directed at pad 26, while in another aspect, the fan 28 is located below pad 26 and fan 28 blows air upward through pad 26. As can be seen, intake air 32 is pulled into housing assembly 12 by fans 28 and is then directed through pad 26 where scented oil 24 is located on pad 26. As intake air 32 traverses pad 26, the outlet air 34 now carries with it the scented oil fragrance into the room. As discussed above with respect to pump 22, the pump controller may also regulate the speed of fans 28. For example, the fans may operate at a given speed based upon the output of pump 22 so that the fans operate at the optimal speed for the amount of fragrance desired. Fans 28 may also oscillate to increase the overall effectiveness of the air freshener if desired so that the fragrant air is forced outward in a wider area.

Referring again to reservoir chamber 14, the reservoir chamber includes a refill opening 36 arranged to receive scented oil from a refill container 38. Once the scented oil within reservoir chamber 14 has been replenished, a refill opening lid 40 can be reinstalled on refill opening 36. The reservoir chamber may be located below dispenser 18 in one aspect, or may be located above the dispenser should a gravity feed system be utilized. Still further, in systems where dispenser 18 is located above the reservoir, pump 22 is also located below dispenser 18. The reservoir container may also include a low level sensor (not shown) for detecting when additional scented liquid must be added and may automatically turn off both the fan and pump if necessary.

Air freshener 10 may be powered in any number of suitable ways, including but not limited to batteries, photovoltaic cells, or standard alternating current through an A/C adapter. Air freshener 10 may include DC operated fans and pumps so that the unit can be portable by operating on batteries as well as being able to run on an A/C adapter. Still further, the unit may include a rechargeable lithium-ion or other compatible battery unit for energy savings and added value to the consumer.

In operation, the user fills up the reservoir chamber and replaces refill opening lid 40. The user also replaces pad 26 if necessary. Pad 26 may become dirty from dust settling or from extensive use. Still further, the user may easily replace pad 26 if he or she wishes to change the scented oil fragrance. The user may then position dispenser 18 by rotating or locating the dispenser head in a particular position. For example, if the user positions the dispenser head directly above a fan, a great amount of fragrance may be dispensed. The user can also control the amount of fragrance emitted into the room by operating the controller to increase or decrease the pump speed and/or the fan speeds. Still further, the controller may have two or three separate functions which may be independently operated. Specifically, the user may be able to control the speed of the fan with a single operation, the speed of the pump with a second operation, and select a fixed or oscillating function of the fan with a third operation. Finally, should the reservoir chamber run out of scented oil, a warning light may be illuminated that tells the user that additional scented oil is required.

In the alternative, the pump and fans may be turned off when the warning light is illuminated to prevent damage to the pump. The controller may also include a timer which can automatically turn off the air freshener after a set amount of time has elapsed or at a particular time.

Implementations of an air freshener and implementing components may be constructed of a wide variety of materials. For example, the components may be formed of: rubbers (synthetic and/or natural) and/or other like materials; glasses (such as fiberglass), carbon-fiber, aramid fiber, any combination thereof, and/or other like materials; polymers such as thermoplastics (such as ABS, Fluoropolymers, Polyacetal, Polyamide; Polycarbonate, Polyethylene, Polysulfone, and/or the like), thermosets (such as Epoxy, Phenolic Resin, Polyimide, Polyurethane, Silicone, and/or the like), any combination thereof, and/or other like materials; composites and/or other like materials; metals, such as zinc, magnesium, titanium, copper, lead, iron, steel, carbon steel, alloy steel, tool steel, stainless steel, brass, tin, antimony, aluminum, any combination thereof, and/or other like materials; alloys, such as aluminum alloy, titanium alloy, magnesium alloy, copper alloy, any combination thereof, and/or other like materials; any other suitable material; and/or any combination of the foregoing thereof.

Some components defining an air freshener implementation may be manufactured simultaneously and integrally joined with one another, while other components may be purchased pre-manufactured or manufactured separately and then assembled with the integral components. The various implementations may be manufactured using conventional procedures as added to and improved upon through the procedures described here.

Accordingly, manufacture of these components separately or simultaneously may involve vacuum forming, injection molding, blow molding, casting, forging, cold rolling, milling, drilling, reaming, turning, grinding, stamping, pressing, cutting, bending, welding, soldering, hardening, riveting, punching, plating, and/or the like. Components manufactured separately may then be coupled or removably coupled with the other integral components in any manner, such as with adhesive, a weld joint, a solder joint, a fastener (e.g. a bolt and a nut, a screw, a rivet, a pin, and/or the like), washers, retainers, wrapping, wiring, any combination thereof, and/or the like for example, depending on, among other considerations, the particular material forming the components.

In places where the description above refers to particular implementations of an air freshener, it should be readily apparent that a number of modifications may be made without departing from the spirit thereof and that these implementations may be applied to other air fresheners. The accompanying claims are intended to cover such modifications as would fall within the true spirit and scope of the disclosure set forth in this document. The presently disclosed implementations are, therefore, to be considered in all respects as illustrative and not restrictive, the scope of the disclosure being indicated by the appended claims rather than the foregoing description. All changes that come within the meaning of and range of equivalency of the claims are intended to be embraced therein.

The invention claimed is:

1. An air freshener comprising:
a housing having a reservoir chamber;
a dispenser;
a pump intermediate the reservoir and the dispenser;
a pad, wherein the dispenser is located above the pad;
at least one fan proximate the pad; and,
wherein the dispenser transfers a scented liquid onto the pad and the at least one fan directs air flow proximate the pad.

2. The air freshener of claim 1 wherein the at least one fan is directed at the pad.

3. The air freshener of claim 1 wherein a channel connects the reservoir chamber and the dispenser.

4. The air freshener of claim 3 wherein the pump is located within the channel.

5. The air freshener of claim 1 wherein the at least one fan is a pair of fans located below the pad.

6. The air freshener of claim 1 wherein the reservoir chamber further comprises a refill opening.

7. The air freshener of claim 1 wherein the pump and the at least one fan are powered by a source selected from the group consisting of batteries, photovoltaic cells, and an alternating current adapter.

8. The air freshener of claim 1 further comprising a controller regulating a speed of the at least one fan and the fluid flow rate of the dispenser.

9. The air freshener of claim 1 wherein the pad is replaceable.

10. The air freshener of claim 1 wherein the reservoir chamber further comprises a low level sensor to turn off the pump when a low level condition is detected.

11. The air freshener of claim 1 wherein the at least one fan oscillates.

12. The air freshener of claim 1 wherein the dispenser is located above the pump.

13. The air freshener of claim 1 wherein the dispenser is located above the reservoir.

14. The air freshener of claim 1 wherein the dispenser is movable.

15. The air freshener of claim 14 wherein moving the dispenser to a position above the at least one fan increases a strength of a scent.

\* \* \* \* \*